United States Patent [19]
Imran

[11] Patent Number: 5,423,771
[45] Date of Patent: Jun. 13, 1995

[54] FLEXIBLE ELONGATE DEVICE HAVING A DISTAL EXTREMITY OF ADJUSTABLE STIFFNESS AND METHOD

[75] Inventor: Mir A. Imran, Palo Alto, Calif.

[73] Assignee: Intelliwire, Inc., Sunnyvale, Calif.

[21] Appl. No.: 147,005

[22] Filed: Nov. 2, 1993

Related U.S. Application Data

[63] Continuation of Ser. No. 983,899, Dec. 1, 1992, abandoned.

[51] Int. Cl.⁶ .............. A61M 25/00; A61M 29/00; A61M 37/00
[52] U.S. Cl. .................. 604/281; 604/96; 604/95
[58] Field of Search .......... 604/95, 96, 280–282; 128/656–658

[56] References Cited

U.S. PATENT DOCUMENTS

| | | | |
|---|---|---|---|
| 4,884,557 | 12/1989 | Takehana et al. | 604/281 |
| 5,090,956 | 2/1992 | McCoy | 128/772 |
| 5,114,402 | 5/1992 | McCoy | 604/95 |
| 5,120,308 | 6/1992 | Hess | 604/95 |

FOREIGN PATENT DOCUMENTS

WO9111213 8/0891 WIPO .

OTHER PUBLICATIONS

"Table of Radio Frequencies", Webster's II New University Dictionary, Houghton Mifflin Co., Boston, Mass. 02108, p. 970.

*Primary Examiner*—C. Fred Rosenbaum
*Assistant Examiner*—Frank Wilkens, III
*Attorney, Agent, or Firm*—Flehr, Hobach, Test, Albritton & Herbert

[57] ABSTRACT

A device comprising a flexible elongate member having proximal and distal extremities. A flexible coil spring is provided having proximal and distal extremities. The proximal extremity of the coil spring is secured to the distal extremity of the flexible elongate member. A shape-memory alloy element is disposed within and extends substantially longitudinally of the coil spring. The shape-memory alloy element has a memory which makes it attempt to assume a straight shape when an electrical current is passed through and heats the same. The shape-memory alloy element also has a stiffness which increases with the temperature of the element. An electrical current supply is provided for supplying an electrical current to the shape-memory alloy element for changing the stiffness of the shape-memory alloy element to thereby stiffen the distal extremity of the flexible elongate member.

12 Claims, 3 Drawing Sheets

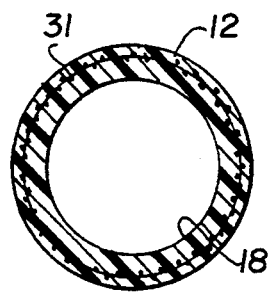
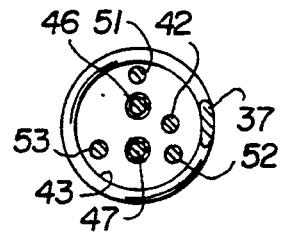
FIG.2  FIG.3
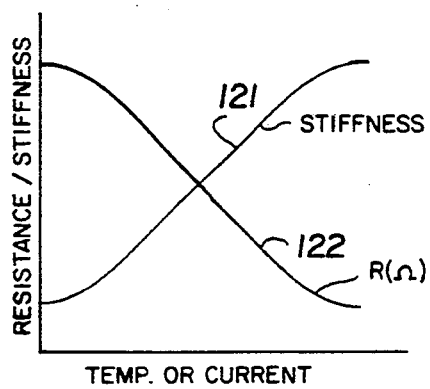
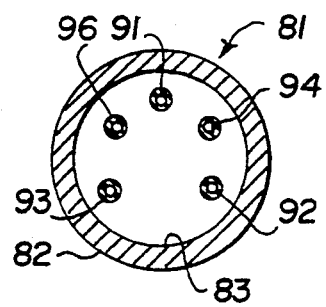
FIG.7  FIG.5
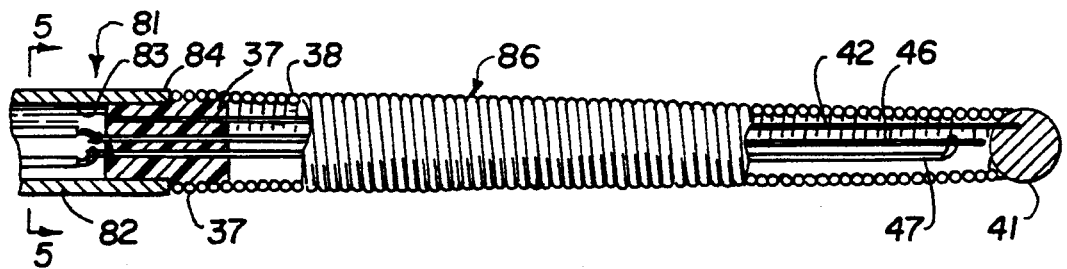
FIG.4

FLEXIBLE ELONGATE DEVICE HAVING A DISTAL EXTREMITY OF ADJUSTABLE STIFFNESS AND METHOD

This is a continuation of application Ser. No. 07/983,899 filed Dec. 1, 1992, now abandoned.

BACKGROUND OF THE INVENTION

This invention relates to a flexible elongate device having a distal extremity of adjustable stiffness and method which is particularly adapted for use as a catheter or a guide wire.

In certain medical procedures, as for example in angioplasty procedures, a catheter having an integral guide wire tip or a guide wire which is able to be deployed through the coronary arteries has been used until a stenosis is reached in the coronary artery that fully or substantially occludes the artery. In the past, it has been difficult if not impossible to negotiate such stenoses in the artery because the tip of the guide wire or catheter is very floppy and typically will buckle under the resistance provided by the stenosis. There is therefore a need for a device which will overcome this difficulty.

In general, it is the object of the present invention to provide a flexible elongate device having a distal extremity of adjustable stiffness and a method to make it possible to penetrate occlusions in vessels of a patient.

Another object of the invention is to provide a device and method of the above character in which the stiffness of the distal extremity can be adjusted during the time that the distal extremity is disposed in the coronary vessel.

Another object of the invention is to provide a device and method of the above character in which the distal extremity is steerable.

Another object of the invention is to provide a device and method of the above character in which a hand-held control mechanism is utilized to adjust the stiffness.

Another object of the invention is to provide a device and method of the above character which can be used in conjunction with the balloon dilatation catheter.

Additional objects and features of the invention will appear from the following description in which the preferred embodiments are set forth in detail in conjunction with the accompanying drawings.

A BRIEF DESCRIPTION OF THE DRAWINGS

FIG. 1 provides a longitudinal cross-sectional view of the distal end of the device.

FIG. 2 provides a transverse cross-sectional view of the distal end proximal of the balloon.

FIG. 3 provides a transverse cross-sectional view of the distal end that is distal of the balloon.

FIG. 4 is a longitudinal cross-sectional view of the distal end of an alternative embodiment.

FIG. 5 is a transverse cross-sectional view of the distal end of the device proximal of the spring coil.

FIG. 7 is a diagram plotting stiffness of the distal end vs. temperature or current.

A DETAILED DESCRIPTION OF THE PREFERRED EMBODIMENT

Figure 1:
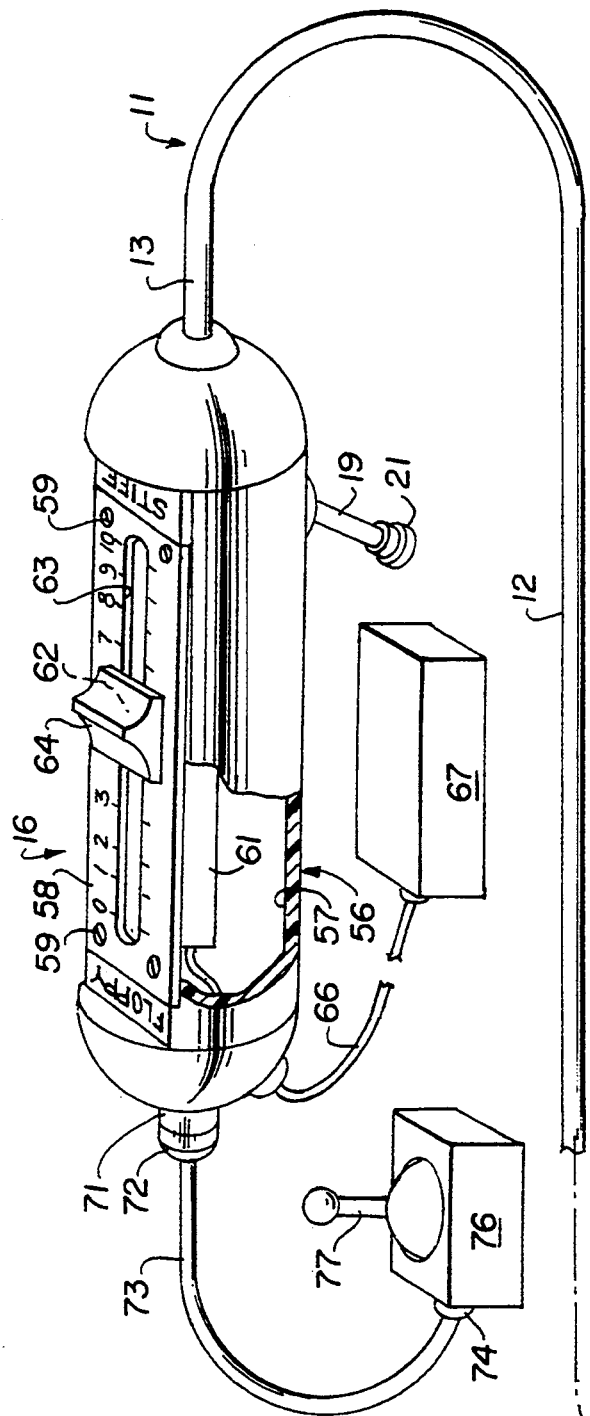
Figure 1:
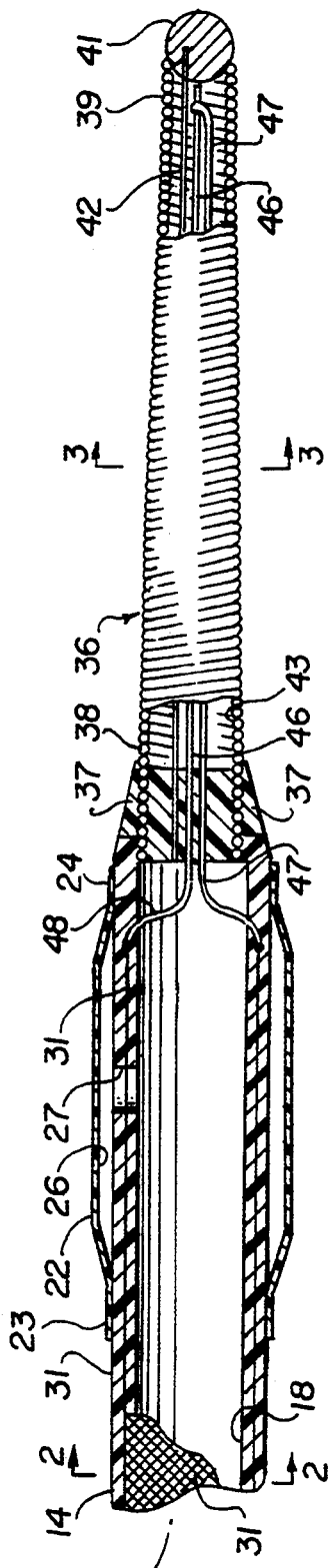

In general, the flexible elongate device having a distal extremity of adjustable stiffness consists of a flexible elongate member having proximal and distal extremities. A flexible coil spring having proximal and distal extremities is provided. Means is provided for securing the proximal extremity of the coil spring to the distal extremity of the flexible elongate member. A shape-memory element is disposed within and extends substantially longitudinally of the coil spring. The shape-memory element has a memory which makes it assume a straight position when electrical current is passed through the same. The shape-memory element also has a stiffness which varies with temperature. Means is provided for supplying electrical current to the shape-memory element for changing the stiffness of the shape-memory element.

More in particular, the device of the present invention as shown in FIGS. 1, 2, 3 and 4 is in the form of a balloon dilatation catheter 11 which consists of a flexible elongate tubular member 12 formed of a suitable material such as plastic that is provided with proximal and distal extremities 13 and 14. A hand-held control mechanism 16 is mounted on the proximal extremity 13. The tubular member 12 is provided with a central lumen 18 free of obstructions extending the length thereof and which is in communication with a flexible tube 19 that extends out of the control mechanism 16 and is provided with a male Luer fitting 21. An inflatable balloon 22 is coaxially mounted on the distal extremity 14 of the flexible elongate tubular member 12 and is provided with proximal and distal extremities 23 and 24 which are adhered to the exterior surface of the flexible elongate tubular member 12 by suitable means such as an adhesive (not shown). The interior 26 of the balloon 22 is in communication with a port 27 provided in the flexible elongate tubular member 12 underlying the interior space 26 to place it in communication with the lumen 18 so that the balloon can be inflated and deflated by the application of a syringe containing a fluid to the fitting 21 during an angioplasty procedure.

A braid 31 is incorporated into the wall of the flexible tubular member 12 and extends the length thereof. The braid 31 serves two purposes. It serves to increase the stiffness of the flexible elongate tubular member 12. It also serves to provide conductors which lead from the proximal extremity 13 to the distal extremity 14 to serve certain functions as hereinafter described. Insulated copper wires can be utilized to make up this braid 31. If a higher conductivity is desired, insulated silver-coated copper wire can be utilized. The braid 31 serves to improve the pushability and the stiffness of the flexible elongate tubular member and also serves to strengthen the tubular member 12.

A guide wire tip 36 is mounted on the distal extremity 14 of the flexible elongate member 12 by suitable means such as an epoxy 37. The tip 36 consists of proximal and distal extremities 38 and 39 and is provided with a slight taper from the proximal extremity to the distal extremity 39. The coil spring 36 is preferably formed of a radiopaque material such as a platinum-tungsten alloy. A rounded ball 41 is provided in the distal extremity 19 and is also of a radiopaque material. A safety ribbon 42 is provided which has one end secured in the epoxy 37 and has the other end secured to the ball 41.

A shape-memory alloy element 46 of a suitable material such as Nitinol extends longitudinally of the conical passage 43 provided within the coil spring 36 and has one end secured in the epoxy 37. The shape-memory element 46 is insulated and has its proximal extremity embedded in the epoxy 37. The distal extremity of the element 46 extends to a point adjacent the ball 41 and is connected to an insulated return conductor 47. The shape-memory alloy element 46 is programmed so that when electrical energy is supplied to the same it wants to become straight and stiff. The shape-memory alloy element 46 can be programmed so that its stiffness will vary over a predetermined temperature range as for example a temperature ranging from 40°-50° C. It has been found that the stiffness variation over this temperature range is very linear. The proximal extremity of the shape-memory alloy element 46 is connected by a conductor 48 to one of the silver-coated copper wires of the braid 31. Similarly the insulated return conductor 47 is connected to another silver-coated copper wire of the braid 31.

Means is provided for steering the distal extremity of the guide wire tip 36 and consists of flexible elongate elements 51, 52 and 53 formed of a suitable material such as Nitinol which has a negative coefficient of expansion. The elements 51, 52 and 53 are circumferentially spaced-apart by a suitable angle as for example 120° and have their distal extremities connected to the return conductor 47. The proximal extremities are embedded in the epoxy 37 and are connected to additional silver-coated copper wires provided in the braid 31 extending to the proximal extremity of the flexible elongate member 12.

It should be appreciated that, if desired, the conductors for the pull elements 51, 52, and 53 can be provided in circumferentially-spaced lumens (not shown) provided in the flexible elongate tubular member 12 with or without the braid 31 therein. Also additional lumens (not shown) can be provided for the conductors 47 and 48 for the shape-memory alloy element 46. Such conductors also could be run through the central lumen 18; however, generally it is desirable to save the central lumen 18 for the passage of fluid for inflating and deflating the balloon 22.

The control mechanism 16 forming a part of the balloon dilatation catheter 11 consists of a housing 56 which is formed of a suitable material such as plastic or metal and is sized so it is adapted to fit in a human hand, as for example with a diameter of 1" and a length of 5-6". The housing 56 is provided with an elongate recess 57 therein which is closed by a cover plate 58 which is secured to the housing 56 by suitable means such as screws 59. A linear potentiometer 61 serving as a control member which represents stiffness is mounted in the space 57 and is provided with a slider 62 movable longitudinally of the potentiometer extending through a longitudinally extending elongate slot 63 provided in the cover plate 58 and is secured to a control member 64 adapted to be grasped by the fingers of the same hand that is holding the control mechanism 16. The potentiometer 61 is connected by a cable 66 to a power supply 67. The potentiometer 61 is also connected to the conductors 47 and 48 through connections made to appropriate silver-coated copper conductors in the braid 31. The utilized conductors in the braid 31 are connected by a cable (not shown) extending through the housing 56 and connected to a connector 71. Connector 71 is connected to another connector 72 which is connected by a cable 73 to a connector 74 connected to a control console 76 provided with a joystick 77.

Another embodiment of a device incorporating the present invention is shown in the form of a guide wire 81. The guide wire 81 can be connected to a control mechanism 16 of the type hereinbefore described. Since a balloon does not form a part of the guide wire, the tube 19 can be omitted. The guide wire 81 is provided with a flexible elongate member 82 which can be in the form of a stainless steel tube 82 often called a hypotube which has a central flow passage or bore 83 extending therethrough from the proximal extremity (not shown) to the distal extremity 84. A guide wire tip 86 substantially identical to the guide wire tip 36 hereinbefore described is secured to the distal extremity 84 of the flexible elongate tubular member 82 with the epoxy 37. In addition, the proximal extremity 38 of the spring 37 can also be secured to the stainless steel tubular member 84 by suitable means such as spot welding. In place of the conductors in the braid 31 utilized for making the connections to the guide wire tip 36, separate conductors 91, 92 and 93 (see FIG. 5) are provided for making contact to the elements 51, 52 and 53 with a negative coefficient of expansion. Separate conductors 94 and 96 are connected respectively to the shape-memory alloy element 46 and the return conductor 47. All of these conductors extend through the small diameter bore 83 provided in the hypotube 82.

Figure 6:
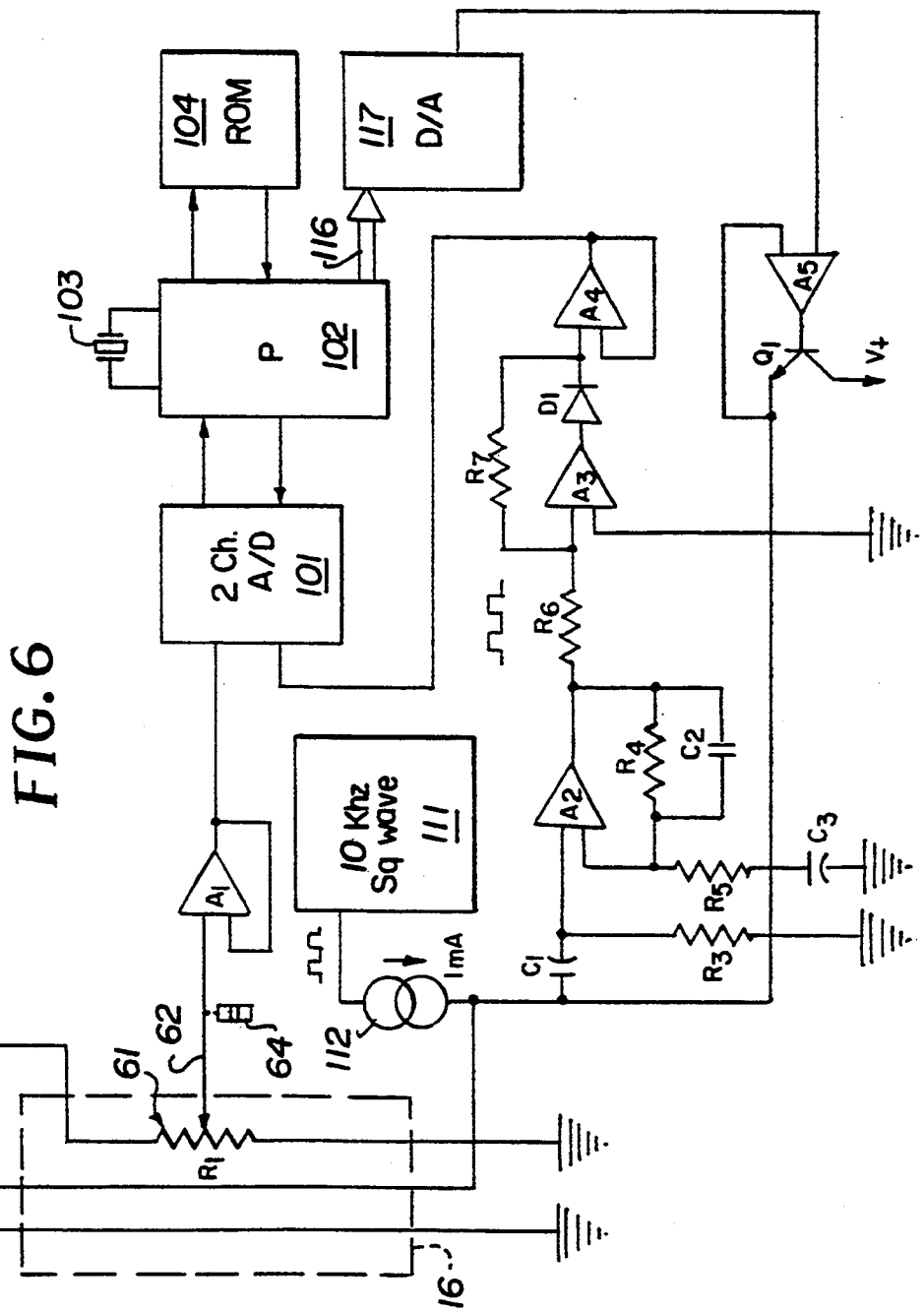
FIG. 6 is a circuit diagram of the device.

The circuitry which is used in the power supply 67 and connected to the potentiometer 61 and to the shape-memory alloy element 46 is shown is FIG. 6. As shown therein, the resistor R1 represents schematically the potentiometer 61. The resistor R1 is connected between ground and a positive voltage identified as V+ through a resistor R2. The wiper arm 62 of the potentiometer 61 picks up a voltage which is proportional to the position of the wiper 62 as controlled by the control member 64. This voltage is supplied to a buffer amplifier A1 which supplies a low impedance output to a two-channel A/D (analog-to-digital) converter 101 which supplies the digital information to a microprocessor 102 controlled by a crystal 103. The microprocessor 102 is programmed by a ROM 104.

Means is provided for measuring the resistance of the shape-memory alloy element 46 and consists of a square wave generator 111 for generating a high frequency as for example 10 kHz which is supplied to a constant current source 112. The constant current source provides a very small amount of current which is insufficient to heat up the shape-memory alloy element 46. The voltage developed across the shape-memory alloy element 46 is supplied through the conductor 47 to the shape-memory alloy element 46. This small current is then capacitively-coupled through a capacitor C1 to an amplifier filter block consisting of an amplifier A2 with the resistor R3 and the capacitor C1 serving as a high-pass filter so that any DC component of the voltage across the shape-memory alloy element 46 will be blocked out. The only interest is in the high frequency current which is used to measure the variance in the resistance value of the shape-memory alloy element 46 which is supplied to the input of an amplifier A2. The amplifier A2 has an output which is coupled to a feedback network consisting of a resistor R4 and a capacitor C2 working in conjunction with the blocking capacitor C3 and the resistor R5. This amplifier-filter combination serves as a band-pass filter with a gain determined by the ratio of the resistors R4 and R5. For example, for low frequency time constant pole is determined by the resistor R5 and capacitor C3. The time constant provided by the resistor R4 and the capacitor C2 determines the location of the pole for the high frequency corner. This amplification and filtering provided by this circuitry serves to eliminate extraneous noise and permits the square wave to pass through without substantial alteration of its shape. This square wave is supplied through a resistor R6 to a full-wave rectifier network consisting of amplifier A3 in series with a diode D1 with a resistor R7 coupled between the input of the amplifier 83 and the output of the diode D1 to provide a full-wave rectified signal. The full-wave rectified signal is supplied to the input of a buffer amplifier A4 whose output is connected to the second channel of the two-channel A/D converter 101. Essentially, the output of the amplifier A4 is a voltage which is proportional to the stiffness of the shape-memory alloy element 46.

Thus, the two signals supplied to the converter 101, one of which is the value supplied by the potentiometer 61 and the other is the value which represents the stiffness of the shape-memory alloy element 46 are sampled by the microprocessor 102 under the control of the ROM 104. The microprocessor 102 then based upon the signal supplied from the potentiometer 61 and the value of the resistance of the shape-memory alloy element 46 utilizes an algorithm supplied by the ROM to calculate the amount of current to be supplied to the shape-memory alloy element 46. This value is supplied through a bus 116 to a D/A (digital-to-analog) converter 117. The output of the D/A (digital-to-analog) converter 117 is supplied to the input of an amplifier A5 and the output of amplifier A5 is connected to a transistor Q1 which serves as a current driver. The current from the current driver Q1 is supplied to the conductor 47 to the shape-memory alloy element 46 to heat up the shape-memory alloy element 46 to stiffen the same.

Operation and use of the balloon dilatation catheter 11 or the guide wire 81 incorporating the present invention may now be briefly described as follows. Depending upon the device desired, either the catheter 11 or the guide wire 81 can be deployed into a coronary artery by inserting the same in a conventional procedure through the femoral artery of the patient and then guiding the guide wire tip 36 or the guide wire tip 86 by the use of the joystick control 76 in the manner described in co-pending application Ser. No. 07/793,858, filed Nov. 18, 1991 now U.S. Pat. No. 5,238,005. The movement of the guide wire tip 36 or the guide wire tip 86 can be observed under fluoroscopy during the procedure. During the time that the catheter 11 or the guide wire 81 is being advanced to the stenosis or lesion in the vessel, typically it is desired to have the tip be very floppy so that it can negotiate tortuous turns in the arterial vessels and also to prevent damage to the walls of the vessels or perforation of the walls of the vessels.

However, in many cases as hereinbefore pointed out with respect to angioplasty procedures, it has been difficult to traverse the lesion or stenosis because it fully occludes or at least substantially occludes the vessel being traversed. Assuming that a lesion or stenosis of this type has been encountered, the catheter 11 or guide wire 81 incorporating the present invention is used to traverse such a lesion or stenosis by increasing the stiffness of the guide wire tip 36 or the guide wire tip 86. To do so, it is merely necessary to use one or more fingers of the hand grasping the control mechanism 16 to engage the control member 64 to move it forwardly from a "zero" or floppy position to a more distal position to cause current to flow into the shape-memory alloy element 46. As soon as this occurs, the shape-memory alloy element 46 is heated and will attempt to straighten itself out and at the same time will increase its stiffness. As soon as the tip 36 or 86 has been stiffened, the cardiologist performing the procedure can then push on the control mechanism 16 to try to advance the guide wire tip 36 of the catheter 11 or the guide wire tip 86 of the guide wire 81 to cross the lesion or stenosis. If this still cannot be accomplished, the control member 64 can be still further advanced to cause further stiffening of the shape-memory alloy element 46. The cardiologist can then utilize the control mechanism 16 to again attempt to push the tips 36 or 86 through the stenosis until they cross the stenosis or lesion. Generally, this additional stiffness which can be created in the shape-memory alloy element 46 should be more than enough to cause the tip 36 or 81 to cross the lesion or stenosis.

The graph shown in FIG. 7 shows how the resistance and stiffness of the shape-memory alloy element 46 changes with respect to temperature or current. Two curves 121 and 122 are shown. Curve 121 represents stiffness versus temperature, whereas curve 122 represents resistivity versus temperature or current. From these two curves 121 and 122 it can be seen that as the temperature of the shape-memory element is increased, the resistance decreases and the stiffness increases. Thus it can be seen that, as pointed out above, as the temperature or current is increased, the stiffness increases.

In accordance with the present invention, when it is desired to provided additional stiffness this can be accomplished by the use of a shape-memory element having a greater cross-sectional area. Also if desired, a plurality of shape-memory elements rather than one can be utilized in tandem or parallel.

By way of example, a guide wire 81 of a suitable diameter, as for example 0.014" could have a guide wire tip 86 having a Shape-memory alloy element 46 therein having a suitable cross-sectional diameter, as for example 0.003 or 0.004". Similarly, for a larger diameter guide wire tip 36 for the catheter 11, the tip could have a diameter ranging from 0.030–0.035" in which there could used a shape-memory alloy element 46 having a diameter ranging from 0.005–0.010".

It is apparent from the foregoing that there has been provided a flexible elongate device having a distal extremity of adjustable stiffness and a method which is particularly applicable for angioplasty procedures as well as for other medical procedures where it becomes necessary to traverse lesions or stenoses which typically have been difficult to traverse with conventional guide wires and catheters.

After the stenosis has been crossed by the guide wire tip 36, the deflated balloon 22 can be advanced into the stenosis and then inflated. In connection with the conventional angioplasty procedure, the balloon will form an enlarged passage through the stenosis. The balloon can then be deflated and removed as in a conventional angioplasty procedure.

With the guide wire 81 crossing the stenosis, it is possible thereafter to pass a conventional balloon dilatation catheter over the guide wire and to cause it to pass through the stenosis to perform an angioplasty procedure.

In connection with the present invention it can be seen that means has been provided for measuring the resistivity of the shape-memory alloy element while it is in use or "on the fly," and that from the information obtained, the microprocessor can be utilized to precisely tailor the current which should be supplied to the shape-memory alloy element to achieve the desired stiffness as determined by the position of the potentiometer.

What is claimed is:

1. In a medical device to be used by the hand for traversing a stenosis or lesion in a vessel of a body, the stenosis or lesion being of a type which fully occludes or at least substantially occludes the vessel so that a conventional guide wire cannot traverse the same, a flexible elongate member having proximal and distal extremities, a flexible coil spring having proximal and distal extremities, means securing the proximal extremity of the flexible coil spring to the distal extremity of the flexible elongate member, said flexible coil spring being sufficiently flexible so that a flexible elongate member can be advanced in the vessel, a shape-memory alloy element carried by the distal extremity of the flexible elongate member, said shape-memory alloy element being disposed within and extending substantially longitudinally of the flexible coil spring and having a memory which makes it attempt to assume a straight shape when heat is supplied to the same, said shape-memory alloy element also having a stiffness in its straight shape which continuously increases with temperature of the shape-memory alloy element and means for supplying an electrical current to supply heat to the shape-memory alloy element for straightening and increasing the stiffness of the shape-memory alloy element and thereby causing the flexible coil spring to be straightened and stiffened by the shape-memory alloy element so that it has the column strength under a force provided to the proximal extremity of the flexible elongate member to traverse the fully occluded or at least substantially occluded stenosis or lesion in the vessel and permit the distal extremity of the flexible elongate member to extent through the stenosis or lesion.

2. In a medical device, a flexible elongate member having proximal and distal extremities, a flexible coil spring having proximal and distal extremities, means securing the proximal extremity of the flexible coil spring to the distal extremity of the flexible elongate member, a shape-memory alloy element carried by the distal extremity of the flexible elongate member, said shape-memory alloy element being disposed within and extending substantially longitudinally of the flexible coil spring and having a memory which makes it attempt to assume a straight shape when heat is supplied to the same, said shape-memory alloy element also having a stiffness which increases with continuously temperature of the shape-memory alloy element and means for supplying an electrical current to supply heat to the shape-memory alloy element for changing the stiffness of the shape-memory alloy element and thereby stiffening the flexible coil spring, said means for supplying an electrical current including a potentiometer and low current, high frequency means for sensing the resistance of the shape-memory alloy element and means for controlling the stiffness of the shape memory alloy element in accordance with the sensed resistance and the desired stiffness as determined by the potentiometer.

3. A device as in claim 1 wherein said device is in the form of a catheter together with a balloon formed on the distal extremity of the catheter and having an interior member, said flexible elongate member having a lumen extending therethrough free of obstructions and means for establishing communication through the flexible elongate member from the lumen to the interior of the balloon for inflating and deflating the balloon.

4. A device as in claim 1 together with a plurality of flexible elongate elements disposed in the distal extremity of the flexible coil spring and having a negative coefficient of expansion and means for supplying electrical energy to the elements having a negative coefficient of expansion to cause bending of the distal extremity of the flexible coil spring.

5. A device as in claim 2 wherein the controlling means includes a control mechanism secured to the proximal extremity of the flexible elongate member, the control mechanism having a housing sized so that it is adapted to be grasped by a human hand and a finger-operated control member carried by the housing adjusting the current supplied by the potentiometer.

6. In a device in the form of a guide wire, a flexible elongate member in the form of a metal tube having proximal and distal extremities, a flexible coil spring having proximal and distal extremities, means securing the proximal extremity of the flexible coil spring to the distal extremity of the flexible elongate member, a shape-memory element carried by the distal extremity of the flexible elongate member, said shape-memory element being disposed within and extending substantially longitudinally of the flexible coil spring and having a memory which makes it attempt to assume a straight shape when heat is supplied to the same, said shape-memory element also having a stiffness which increases with temperature of the shape-memory element and means for supplying an electrical current to supply heat to the shape-memory element for changing the stiffness of the shape-memory element and thereby stiffening the flexible coil spring, said means for supplying an electrical current including a control mechanism secured to the proximal extremity of the flexible elongate member, the control mechanism having a housing adapted to be grasped by a human hand and a finger-operated control member carried by the housing, a linear potentiometer mounted within the housing and having a slider and means connecting said slider to said control member.

7. A device as in claim 1 together with a balloon mounted on the distal extremity of the flexible elongate member, said flexible elongate member having a lumen extending therethrough and means provided in the flexible elongate member for establishing communication between the lumen and the interior of the balloon to permit inflation and deflation of the balloon.

8. A device as in claim 1 together with a plurality of circumferentially spaced-apart elements having a negative coefficient of expansion disposed within the flexible coil spring and electrical means for supplying current to the elements having a negative coefficient of expansion for steering the distal extremity of the flexible coil spring, 9. A device as in claim 8 wherein said device is in the form of a guide wire and wherein said flexible elongate tubular member is formed of a metal tube.

10. In a medical device, a flexible elongate member having proximal and distal extremities, a flexible coil spring having proximal and distal extremities, means securing the proximal extremity of the flexible coil spring to the distal extremity of the flexible elongate member, a shape-memory element carried by the distal extremity of the flexible elongate member, said shape-memory element being disposed within and extending substantially longitudinally of the flexible coil spring and having a memory which makes it attempt to assume a straight shape when heat is supplied to the same, said shape-memory element also having a stiffness which increases with temperature of the shape-memory element, means for supplying an electrical current to supply heat to the shape-memory element for changing the stiffness of the shape-memory element and thereby stiffening the flexible coil spring, a plurality of circumferentially spaced-apart elements having a negative coefficient of expansion disposed within the flexible coil spring and electrical means for supplying current to the elements having a negative coefficient of expansion for steering the distal extremity of the flexible coil spring, said flexible elongate tubular member in the form of a metal tube being provided with a bore extending therethrough and conductors extending through said bore and connected to said elements having a negative coefficient of friction and also to said shape-memory element.

11. A method for penetrating a fully occluded or substantially fully occluded stenosis or lesion in a vessel in a human body which is incapable of being traversed by a conventional guide wire, the method utilizing a flexible elongate member having proximal and distal extremities and including a shape memory alloy element disposed in the distal extremity and being programmed with a memory so that when heat is supplied to the shape memory alloy element it becomes straight and stiff and when heat is not supplied it becomes relatively floppy, introducing the flexible elongate element into the vessel so that the distal extremity is in the vicinity of the fully occluded or substantially fully occluded stenosis or lesion to be traversed, supplying heat to the shape memory alloy element to cause straightening and stiffening of the distal extremity of the flexible elongate member and thereby provide sufficient columnar strength to the distal extremity of the flexible elongate member so that it can penetrate the fully occluded or substantially fully occluded stenosis or lesion and applying a force by hand to the proximal extremity of the flexible elongate member to advance the straightened and stiffened distal extremity of the flexible elongate member so that it traverses the fully occluded or substantially fully occluded stenosis or lesion.

12. In a balloon dilatation catheter to be used by the hand for traversing a stenosis or lesion in a vessel of a body, the stenosis or lesion being of a type which fully occludes or at least substantially occludes the vessel so that a conventional guide wire cannot traverse the same, a flexible elongate member having proximal and distal extremities, an inflatable balloon formed on the distal extremity of the flexible elongate member and having an interior, said flexible elongate member having a lumen extending therethrough free of obstructions, means for establishing communication through the flexible elongate member from the lumen to the interior of the balloon for inflating and deflating the balloon and guiding means secured to the distal extremity of the flexible elongate member distal of the balloon, said guiding means comprising a flexible coil spring having proximal and distal extremities, means securing the proximal extremity of the flexible coil spring to the distal extremity of the flexible elongate member, said flexible coil spring being sufficiently flexible so that the flexible elongate member can be advanced in the vessel, a shape-memory element carried by the distal extremity of the flexible elongate member, said shape-memory element being disposed within and extending substantially longitudinally of the flexible coil spring and having a memory which makes it attempt to assume a straight shape when heat is supplied to the same, said shape-memory element also having a stiffness in its straight shape which continuously increases with temperature of the shape-memory element and means for supplying an electrical current to supply heat to the shape-memory element for straightening and increasing the stiffness of the shape-memory element and thereby causing the flexible coil spring to be straightened and stiffened by the shape-memory, element so that it has the column strength under a force provided to the proximal extremity of the flexible elongate member to traverse the fully occluded or at least substantially occluded stenosis or lesion in the vessel and permit the inflatable balloon to extend through the stenosis or lesion.

* * * * *